United States Patent
Ruby et al.

(10) Patent No.: US 9,993,823 B2
(45) Date of Patent: Jun. 12, 2018

(54) LABORATORY SPECIMEN TRAY

(71) Applicants: Stephen G. Ruby, Burr Ridge, IL (US); Sharon Jeanne Lang, Wauconda, IL (US)

(72) Inventors: Stephen G. Ruby, Burr Ridge, IL (US); Sharon Jeanne Lang, Wauconda, IL (US)

( * ) Notice: Subject to any disclaimer, the term of this patent is extended or adjusted under 35 U.S.C. 154(b) by 0 days. days.

(21) Appl. No.: 15/232,317

(22) Filed: Aug. 9, 2016

(65) Prior Publication Data

US 2018/0043365 A1    Feb. 15, 2018

(51) Int. Cl.
   *B01L 9/00* (2006.01)
   *B01L 3/00* (2006.01)

(52) U.S. Cl.
   CPC ........ *B01L 9/00* (2013.01); *B01L 3/54* (2013.01); *B01L 2300/021* (2013.01); *B01L 2300/0809* (2013.01)

(58) Field of Classification Search
   CPC ........................................................ B01L 9/00
   See application file for complete search history.

(56) References Cited

U.S. PATENT DOCUMENTS

| | | | | |
|---|---|---|---|---|
| 3,582,285 A | * | 6/1971 | Hamilton et al. | .... B01L 3/5085 206/461 |
| 4,195,059 A | * | 3/1980 | Whitcher | ............... B01L 9/54 206/459.5 |
| 5,590,782 A | * | 1/1997 | Haber | .................... A61J 1/16 206/528 |
| 6,536,219 B2 | * | 3/2003 | Peters | .................... G01N 1/42 165/80.1 |

* cited by examiner

*Primary Examiner* — Jyoti Nagpaul

(57) ABSTRACT

A laboratory specimen tray for the organization of medical and scientific specimens for improving continuity of case/patient identification and reduction in the mislabeling or mixing of specimens between patients is provided. The specimen tray may be an elongated body of material that forms various voids for securing various types of specimen containers and associated paperwork. An upper surface of the specimen tray provides a distinct demarcation, such as one of a plurality of colors, so that two specimens of the same type are never next to each other in a laboratory setting, further preventing the possibility of specimen/patient mix ups. This separation makes sure that a cassette during sectioning by the technologist is not accidentally cut and placed on the wrong patient slide.

1 Claim, 3 Drawing Sheets

LABORATORY SPECIMEN TRAY

BACKGROUND OF THE INVENTION

The present invention relates to trays and, more particularly, to a laboratory specimen tray for the organization of medical and scientific specimens for improving continuity of case/patient identification and reduction in the mislabeling or mixing of specimens between patients.

On any given day, across the globe, millions of patient specimens are submitted to laboratories for testing. Since the beginning of laboratory medicine, however, a consistent problem that has plagued this system, and that problem being lost, missing, misplaced, mislabeled specimens or mixing of two or more patients' specimens. This is an issue that has been identified by various agencies as a source of significant patient error. Despite reasonable care by healthcare workers, one patient's specimens are occasionally mixed with another patient's case, for example when the tissue processing cassettes or other containers are mislabeled, which has the potential for causing patients harm or even death.

Typically, specimen(s) from a patient, upon receipt in the laboratory, are accessioned in the laboratory information system, and tissue processing cassettes are labeled for the specimen(s). Those elements (requisition, patient specimen (s) and tissue cassette(s)) are then added to the queue of patient specimens for processing by the pathologist (or designee) in a grossing area of the pathology lab awaiting submission for testing. This queue typically consists of multiple patient specimens, and their associated labeled tissue cassettes and requisition, are placed, in order, in a loose manner in line with other patient cases. Because they are loose, and not held together by a mechanical device, different patient cases can accidentally be mixed with other patient case(s) awaiting processing, resulting in specimens being mishandled and mixed up with another patient's specimens. If the patients have similar specimens (i.e. both patients having tissue biopsies from the same location, such as colon or stomach) the ability to identify such mixing of cases by the pathologist reading the completed slides is nearly completely absent, even if the patient cross identification is identified, (i.e. two different sources of specimens, such as colon biopsy and cervical biopsy).

Currently, there are no devices that provide this type of protection. Every specimen is just simply placed in a queue on a counter, which is where the inadvertent mixing occurs. Because there are no devices helping to separate cases completely, the specimen/patient containers are then allowed to move into the area of the next patient providing the wrong diagnosis.

As can be seen, there is a need for a laboratory specimen tray for the organization of medical and scientific specimens for improving continuity of case/patient identification and reduction in the mislabeling or mixing of specimens between patients.

SUMMARY OF THE INVENTION

In one aspect of the present invention, a laboratory specimen tray for the organization of medical and scientific specimens includes an elongated body of material having opposing lower and upper surfaces; an elongated slot formed along the upper surface so as to extend substantially the full length thereof; at least one circular recess formed along the upper surface; at least one rectangular cavity formed along the upper surface; and an identification marking is provided along the upper surface.

In another aspect of the present invention, the laboratory specimen tray for the organization of medical and scientific specimens includes an elongated body of material having opposing lower and upper surfaces wherein the upper surface is not coextensive with the lower surface, forming an overhanging flange on each of the opposing ends of the elongated body; an elongated slot formed along the upper surface so as to extend substantially the full length thereof; at least one circular recess formed along the upper surface; at least one gripping circular recess formed along the upper surface, wherein each gripping circular recess provides a circumferential grip insert extending into said gripping circular recess; at least one rectangular cavity formed along the upper surface, wherein each rectangular cavity is dimensioned to secure a tissue processing cassette therein; and an identification color is provided along the upper surface, wherein each of the at least one circular recess is aligned with each other, and wherein each of the at least one rectangular cavity is aligned with each other.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a laboratory specimen tray for the organization of medical and scientific specimens for improving continuity of case/patient identification and reduction in the mislabeling or mixing of specimens between patients. The specimen tray may be an elongated body of material that forms various voids for securing various types of specimen containers and associated paperwork. An upper surface of the specimen tray provides a distinct demarcation, such as one of a plurality of colors, so that two specimens of the same type are never next to each other in a laboratory setting, further preventing the possibility of specimen/patient mix ups.

Figure 1:
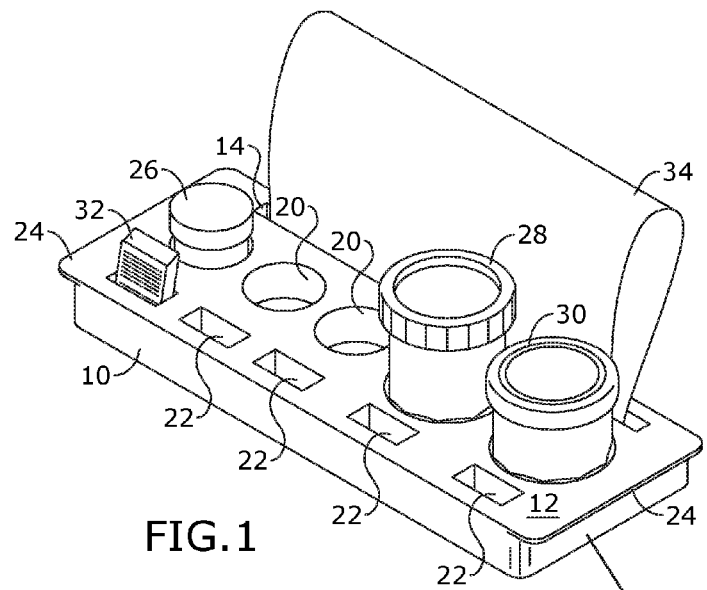
FIG. 1 is a perspective view of an exemplary embodiment of the present invention, shown in use.
Figure 2:
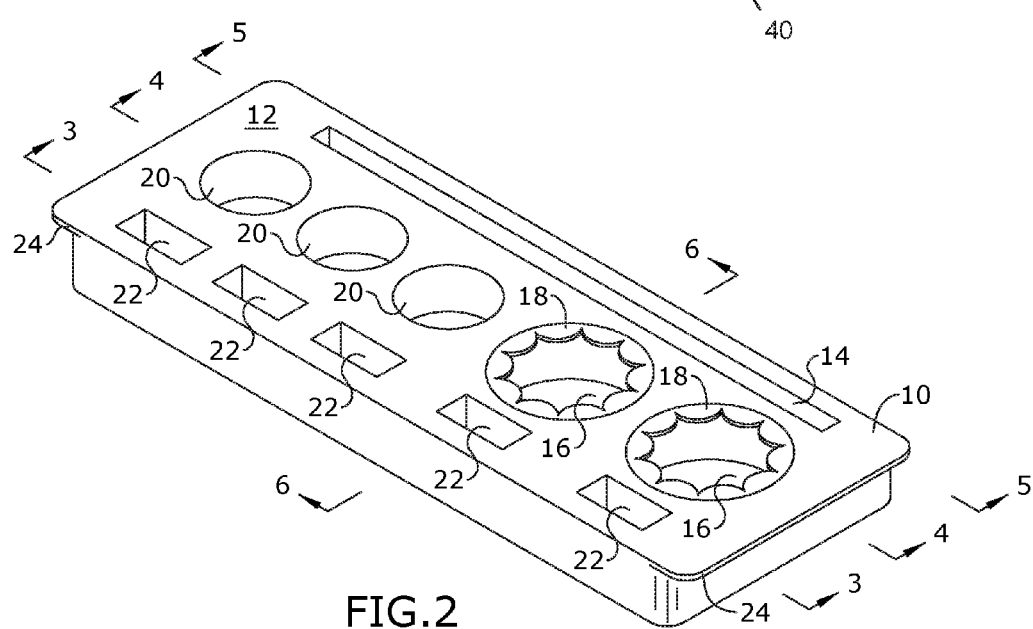
FIG. 2 is a perspective view of an exemplary embodiment of the present invention.
Figure 3:
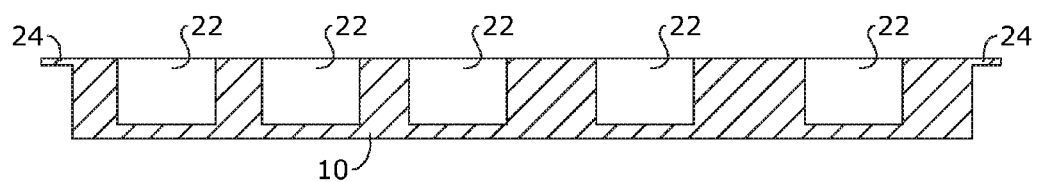
FIG. 3 is a section view of an exemplary embodiment of the present invention, taken along line 3-3 of FIG. 2.
Figure 4:
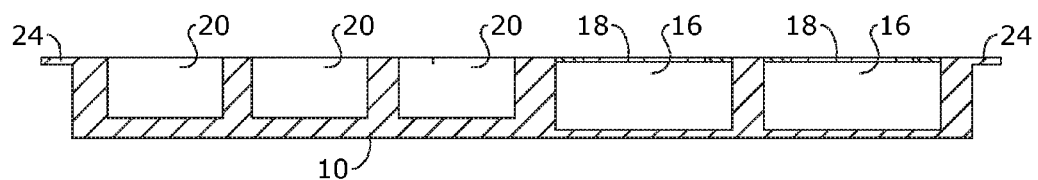
FIG. 4 is a section view of an exemplary embodiment of the present invention, taken along line 4-4 of FIG. 2.
Figure 5:
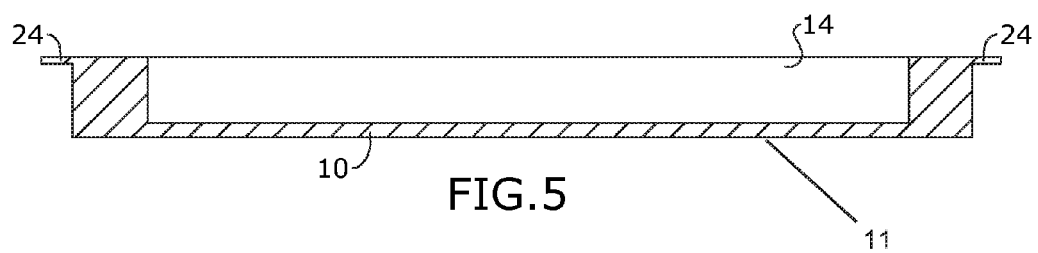
FIG. 5 is a section view of an exemplary embodiment of the present invention, taken along line 5-5 of FIG. 2.
Figure 6:
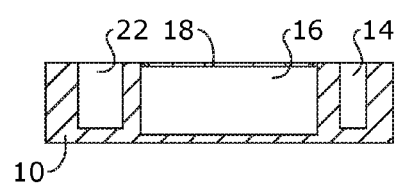
FIG. 6 is a section view of an exemplary embodiment of the present invention, taken along line 6-6 of FIG. 2.
Figure 7:
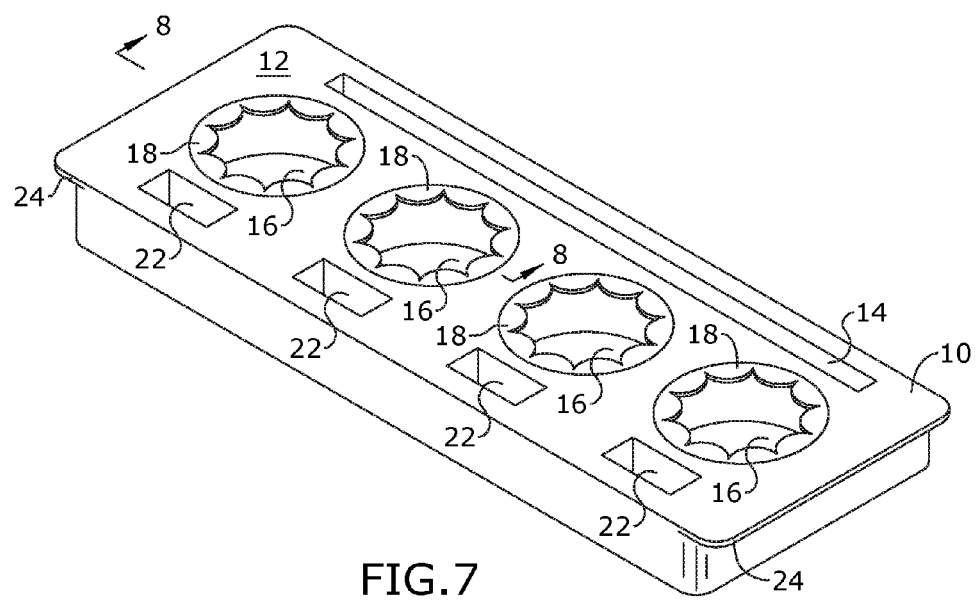
FIG. 7 is a perspective view of an exemplary embodiment of the present invention.
Figure 8:
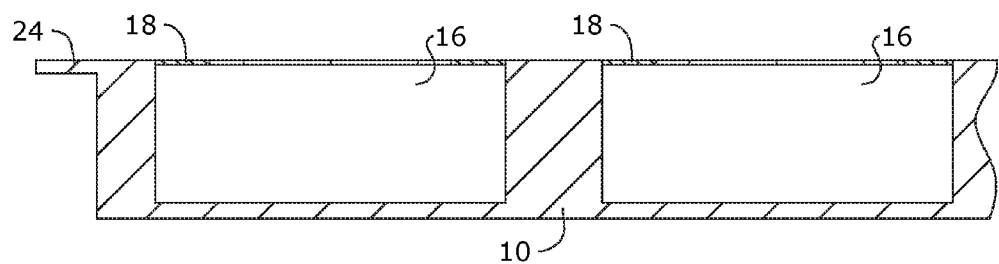
FIG. 8 is a section view of an exemplary embodiment of the present invention, taken along line 8-8 of FIG. 7.

Referring to FIGS. 1 through 8, the present invention may include a specimen tray 10. The specimen tray 10 may include an elongated body 40 of material providing a lower surface 11 and an opposing upper surface 12, wherein the upper surface extends farther than the lower surface 11 so as to provide an overhanging flange 24 on each of the opposing ends of the specimen tray 10, as illustrated in FIG. 2. Each overhanging flange 24 provides a grip for a user to manipulate and move said specimen tray 10.

It should be noted that the specimen tray 10 may be shaped or formed in any configuration, so long as the specimen tray 10 functions in accordance with the present invention as described herein. The specimen tray 10 may be made of any material that can repeatedly be bent or dropped during handling without fracturing, such as polyethylene, polypropylene, vinyl, nylon, rubber, leather, various impregnated or laminated fibrous materials, various plasticized materials and the like.

The lower surface 11 may be generally flat so as to provide a convenient surface to rest the specimen tray 10 on a supporting surface, such as a gross table or another surface provided by a laboratory station. The upper surface 12 may provide one or more of a plurality of identification markings, such as colors. In the case of using colors, the identification markings may either be through (colored) material type, through material receptive to various forms of color printing or the like, whereby various colors can be used to separate the different types of specimens, and therefore making sure two specimens of the same type are never next to each other in a laboratory setting, further preventing the possibility of specimen/patient mix ups.

The specimen tray 10 may provide various voids formed from the elongated body 40. The elongated body 40 may form an elongated slot 14 extending substantially the full length of the elongated body 40, wherein the dimensions (width and depth) of the elongated slot 14 may be adapted so as to secure at least one sheet of paper 34 therein, as illustrated in FIG. 1. The elongated body 40 may form a plurality of circular recesses 16 and 20. In certain embodiments, the plurality of circular recesses 16 and 20 may be positioned generally parallel with each other. Some circular recesses 16 may provide circumferential grip inserts 18 that extend partially into the recess. The circumferential grip inserts 18 may be made of elastic material taking a wave-like shape so as to be biased in a first position relatively parallel with an opening to the associated recess 20. Thereby, specimen jars 26, 28, 30, even non-circular ones, having a periphery less than the circumference of the associated circular recess 20 would be securely retained therein, as the circumferential grip inserts 18 would deform sufficiently to receive said specimen jars 26, 28, 30, yet its biasing would facilitate a snug grip thereon. The elongated body 40 may form a plurality of rectangular cavities 22, each dimensioned and adapted to retain a cassette 32, such as square tissue cassette used in medical reviews or the like. The plurality of rectangular cavities 22 may be positioned generally parallel with each other.

In certain embodiments, void positions may not be the same on a given specimen tray. For example, depending on the need of the laboratory, various void positions may be customized, such as for allowing for the securing of a formalin jar, a test tube, or the like. Therefore, the shape of the at least one formed void and the at least one container may be changed.

A method of using the present invention may include the following. The specimen tray 10 disclosed above may be provided. A user may place the specimen/sample containers 26-32 and associated paperwork 34 of a patient in the appropriate void/cavity/slot/recess formed in the elongated body 40, and because of the identification markings (e.g., color coding) no two patients' specimens would be placed next to each other; this separation makes sure that, for example, a cassette during sectioning by the technologist is not accidentally cut and placed in another patient's slide.

The laboratory specimen tray 10 may improve patient safety by reducing mislabeled or mixed up patient specimens, resulting in an associated reduction in patient harm and malpractice related events. The organization of the laboratory specimen tray may also improve efficiency of the laboratory services resulting in cost reductions. The laboratory specimen tray may also help prevent potential risk to laboratory staff to biologic and chemical exposures from minor spills.

It should be understood, of course, that the foregoing relates to exemplary embodiments of the invention and that modifications may be made without departing from the spirit and scope of the invention as set forth in the following claims.

What is claimed is:

1. A laboratory specimen tray kit, comprising:
   an elongated body of material having opposing lower and upper surfaces;
   an elongated slot formed along the upper surface so as to extend substantially the full length thereof;
   a plurality of circular recesses formed along the upper surface;
   a plurality of rectangular cavities formed along the upper surface, each circular recess operatively aligns with one of the plurality of rectangular cavities, and wherein each rectangular cavity is dimensioned to accommodate a square tissue cassette;
   an identification marking is provided along the upper surface;
   a requisition paperwork secured in the elongated slot;
   a container disposed in at least one of the plurality of circular recesses, wherein each container contains a specimen associated with the requisition paperwork; and
   a square tissue cassette operatively aligned with each container, wherein each square tissue cassette is disposed in one of the plurality of rectangular cavities.

* * * * *